(12) United States Patent
Chenal

(10) Patent No.: US 11,229,552 B1
(45) Date of Patent: Jan. 25, 2022

(54) APPARATUS AND METHOD FOR AN EARPIECE DEVICE

(71) Applicant: JMJ Holdings, LLC, Frederic, WI (US)

(72) Inventor: David M. Chenal, Frederic, WI (US)

(73) Assignee: JMJ Holdings, LLC, Frederic, WI (US)

( * ) Notice: Subject to any disclaimer, the term of this patent is extended or adjusted under 35 U.S.C. 154(b) by 0 days.

(21) Appl. No.: 17/327,582

(22) Filed: May 21, 2021

Related U.S. Application Data

(62) Division of application No. 29/769,169, filed on Feb. 3, 2021.

(51) Int. Cl.
*A61F 11/08* (2006.01)

(52) U.S. Cl.
CPC ......... *A61F 11/08* (2013.01); *A61F 2011/085* (2013.01)

(58) Field of Classification Search
CPC .... A61F 11/08; A61F 2011/085; A61F 11/12; A61F 11/00; A61F 11/06; A61F 2002/183; A61F 2/18; H04R 2460/13; H04R 25/606; H04R 1/1016; H04R 2410/05; H04R 31/00; H01L 2224/48091; H01L 2924/00014; Y10T 29/49005; Y10T 29/43; Y10T 29/4908; Y10T 29/49002; Y10T 82/2593

See application file for complete search history.

(56) References Cited

U.S. PATENT DOCUMENTS

| | | | |
|---|---|---|---|
| 5,113,967 A * | 5/1992 | Killion | A61F 11/08 181/132 |
| 6,148,821 A * | 11/2000 | Falco | H04R 1/1016 128/864 |
| 7,236,605 B2 | 6/2007 | Oliviera et al. | |
| 7,743,771 B2 | 6/2010 | Falco | |
| 8,161,975 B2 | 4/2012 | Turdjian | |
| 8,327,973 B2 | 12/2012 | Parish et al. | |
| 8,596,279 B2 | 12/2013 | Falco | |
| 9,603,746 B2 | 3/2017 | Chenal | |
| 10,440,459 B2 | 10/2019 | Smith et al. | |
| 10,940,043 B2 | 3/2021 | Chenal | |
| 2010/0195860 A1 * | 8/2010 | Becker | H04R 1/1016 381/371 |

* cited by examiner

*Primary Examiner* — Ophelia A Hawthorne
(74) *Attorney, Agent, or Firm* — Charles A. Lemaire; Jonathan M. Rixen; Lemaire Patent Law Firm, P.L.L.C.

(57) ABSTRACT

The present invention provides a sound attenuation system that includes a base having a first portion on an emitter end of the base and a second portion on a receiver end of the base, wherein the first portion has a first longitudinal axis, wherein the second portion has a second longitudinal axis, and wherein the first longitudinal axis is at a first angle to the second longitudinal axis; an adapter having a first end and a second end; a sound-attenuation plug, wherein the first end of the adapter is configured to couple to the sound-attenuation plug, and wherein the second end of the adapter is configured to couple to the first portion of the base; and a receiver-end component configured to insert into the second portion of the base.

20 Claims, 12 Drawing Sheets

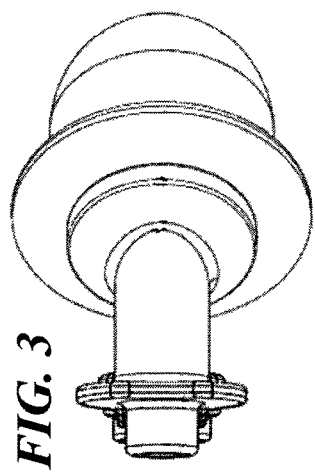
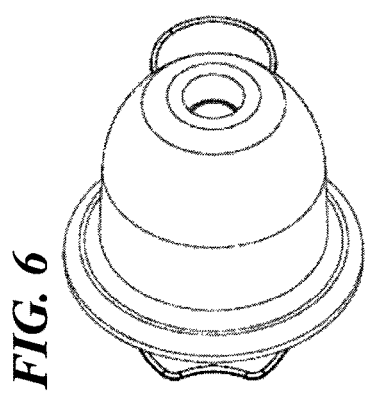
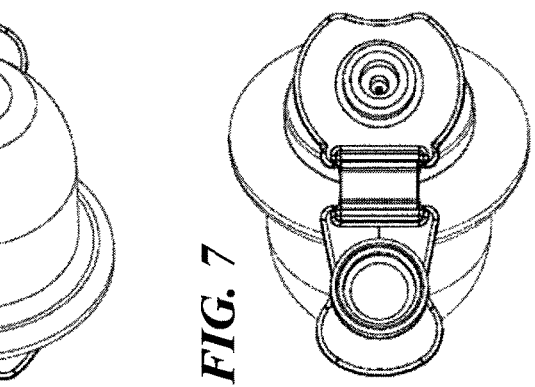
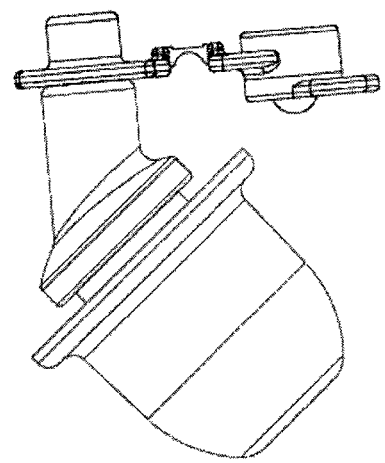
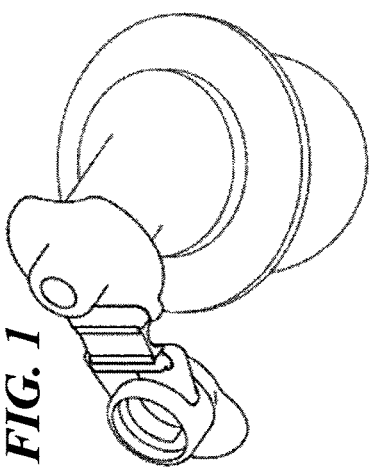
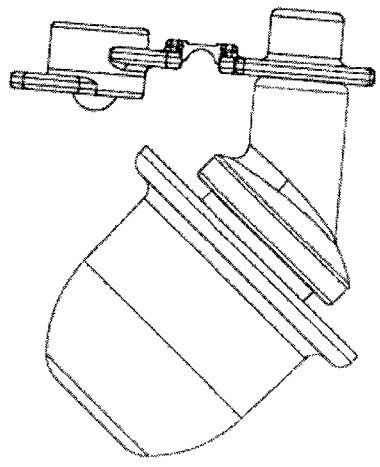

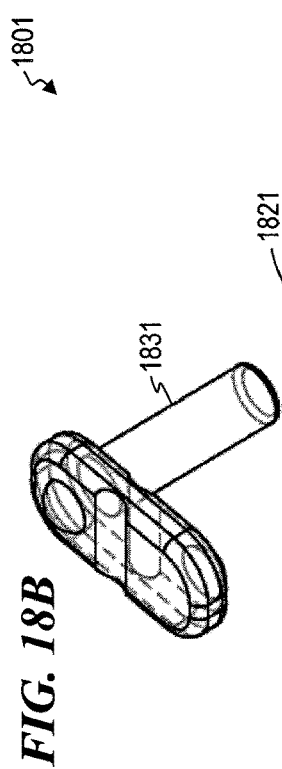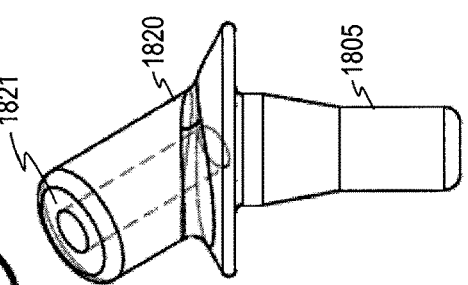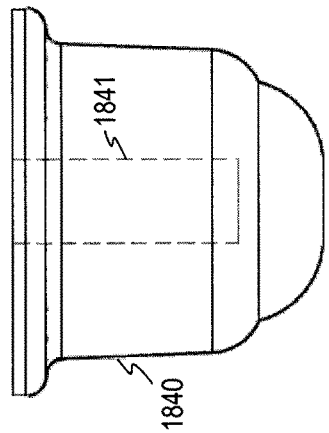
FIG. 18A
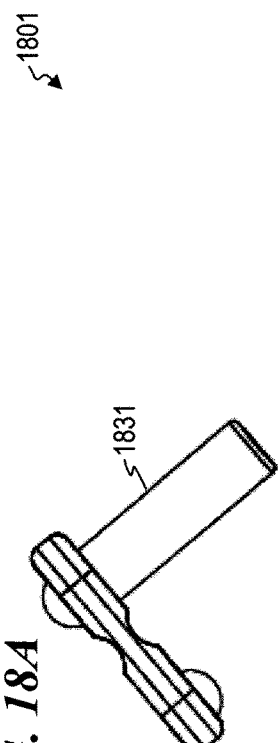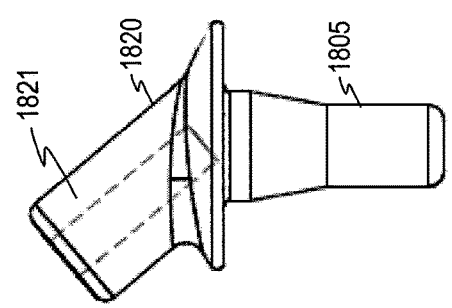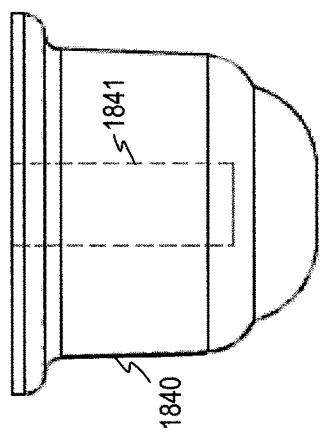
FIG. 18B

APPARATUS AND METHOD FOR AN EARPIECE DEVICE

CROSS-REFERENCE TO RELATED APPLICATIONS

This application is a divisional application of U.S. Design patent application No. 29/769,169 filed Feb. 3, 2021, which is incorporated herein by reference in its entirety.

This application is related to:
- PCT Patent Application No. PCT/US2020/066494, filed Dec. 21, 2020 by JMJ Holdings, LLC, titled "APPARATUS AND METHOD FOR AN EARPIECE-FOAM SHAPING/SIZING TOOL AND CONTAINER" (published as WO 2021/133747);
- U.S. Design patent application No. 29/718,377, filed Dec. 23, 2019 by JMJ Holdings, LLC, titled "EARPIECE-FOAM SIZING TOOL";
- U.S. patent application Ser. No. 15/566,699, filed Oct. 14, 2017 by JMJ Holdings, LLC, titled "SOUND ATTENUATION APPARATUS AND METHOD" (which issued as U.S. Pat. No. 10,940,043 on Mar. 9, 2021); and
- U.S. patent application Ser. No. 15/130,417, filed Apr. 15, 2016 by JMJ Holdings, LLC, titled "SOUND ATTENUATION" (which issued as U.S. Pat. No. 9,603,746 on Mar. 28, 2017); each of which is incorporated herein by reference in its entirety.

FIELD OF THE INVENTION

The present invention relates to devices and methods for earpiece devices, and in particular to a system and method for earpieces configured to fit into the user's ear with improved comfort and flexibility.

BACKGROUND OF THE INVENTION

U.S. Pat. No. 7,236,605 by Robert J. Oliveira et al. issued on Jun. 26, 2007 with the title "User disposable sleeve for use within the ear canal", and is incorporated herein by reference.

U.S. Pat. No. 7,743,771 by Robert N. Falco issued on Jun. 29, 2010 with the title "Earplug with articulating stem and locking features", and is incorporated herein by reference.

U.S. Pat. No. 8,161,975 by Crest Turdijian. issued on Apr. 24, 2012 with the title "Dual mode impulse noise protecting earplug (D-182)", and is incorporated herein by reference.

U.S. Pat. No. 8,327,973 by William Parish et al. issued on Dec. 11, 2012 with the title "Foam compositions with enhanced sound attenuation", and is incorporated herein by reference.

U.S. Pat. No. 8,596,279 by Robert N. Falco issued on Dec. 3, 2013 with the title "Offset stem for earplug and earplug formed therewith", and is incorporated herein by reference.

U.S. Pat. No. 10,440,459 by Richard C. Smith et al. issued on Oct. 8, 2019 with the title "Ergonomic earpiece", and is incorporated herein by reference.

There remains a need for an improved earpiece device.

SUMMARY OF THE INVENTION

The present invention provides a sound attenuation system that includes a base having a first portion on an emitter end of the base and a second portion on a receiver end of the base, wherein the first portion has a first longitudinal axis, wherein the second portion has a second longitudinal axis, and wherein the first longitudinal axis is at a first angle to the second longitudinal axis; an adapter having a first end and a second end; a sound-attenuation plug, wherein the first end of the adapter is configured to couple to the sound-attenuation plug, and wherein the second end of the adapter is configured to couple to the first portion of the base; and a receiver-end component configured to insert into the second portion of the base.

BRIEF DESCRIPTION OF THE FIGURES

FIG. 1 is a perspective view of an earpiece device, according to some embodiments of the present invention.

FIG. 2 is a back view of the earpiece device, according to some embodiments of the present invention.

FIG. 3 is a front view of the earpiece device, according to some embodiments of the present invention.

FIG. 4 is a left-side view of the earpiece device, according to some embodiments of the present invention.

FIG. 5 is a right-side view of the earpiece device, according to some embodiments of the present invention.

FIG. 6 is a bottom view of the earpiece device, according to some embodiments of the present invention.

FIG. 7 is a top view of the earpiece device, according to some embodiments of the present invention.

FIG. 17B-1 is a side view of an angled earpiece system 1702, according to some embodiments of the present invention.

FIG. 17B-2 is a schematic cross-sectional diagram of angled earpiece system 1702, according to some embodiments of the present invention.

FIG. 18A is an exploded side view of an angled earpiece system 1801, according to some embodiments of the present invention.

FIG. 18B is an exploded and rotated side view of angled earpiece system 1801, according to some embodiments of the present invention.

DETAILED DESCRIPTION OF THE INVENTION

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter to material associated with such marks.

Figure 17A:
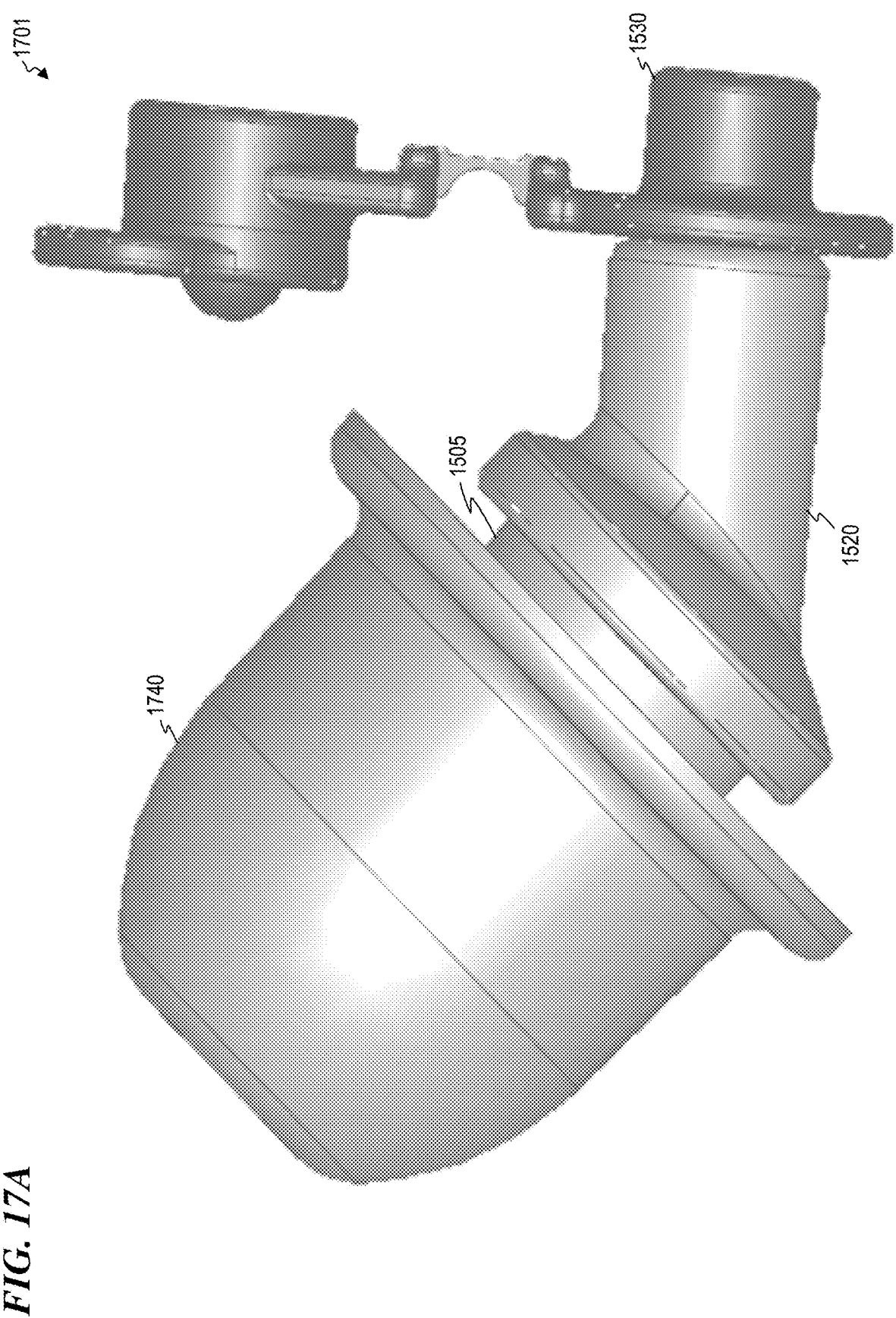
FIG. 17A is a side view of an angled earpiece system 1701, according to some embodiments of the present invention.
Figures 1, 17B:
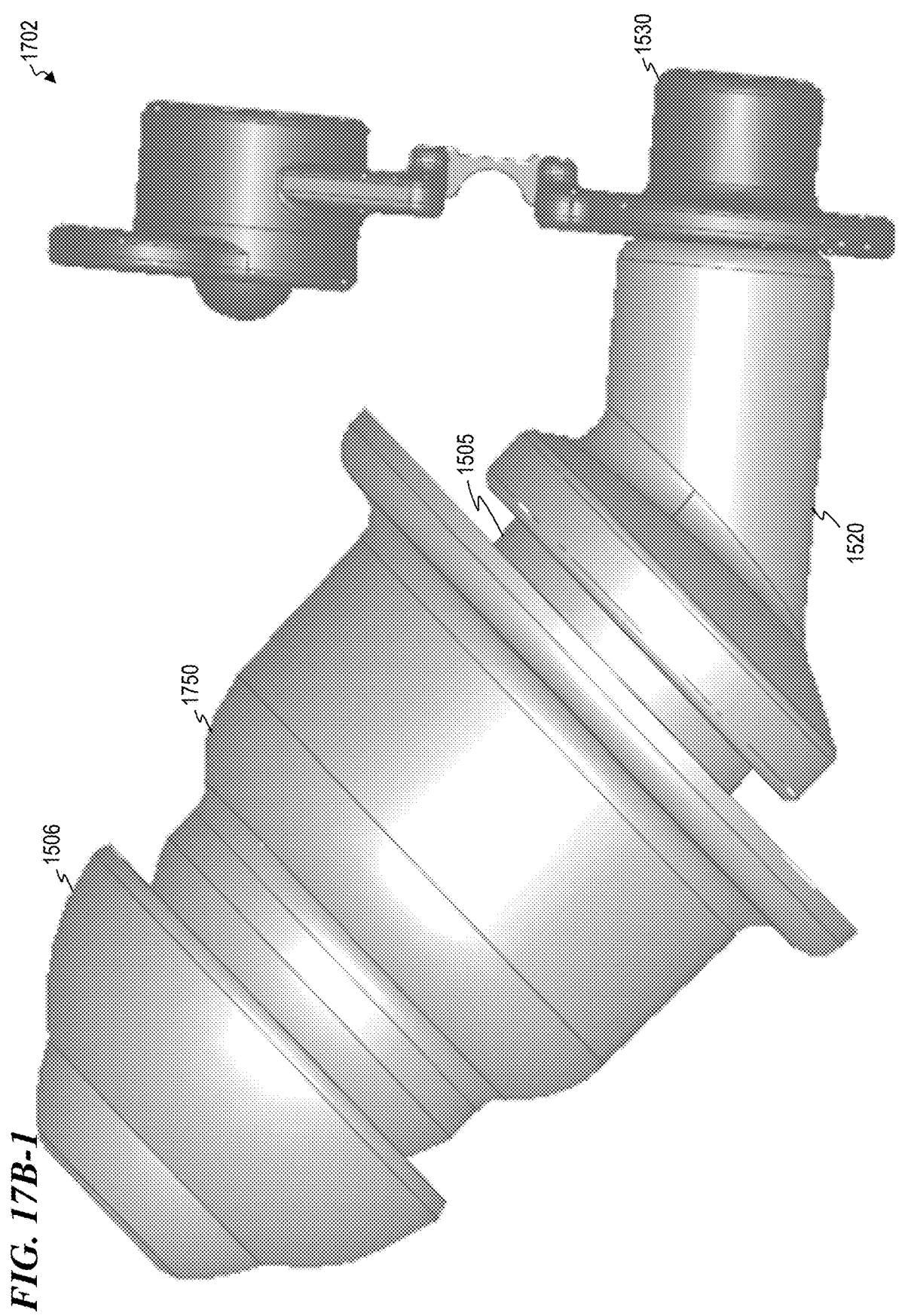

FIG. 1 is a perspective view of an earpiece device, according to some embodiments of the present invention.

Figures 2, 17B:
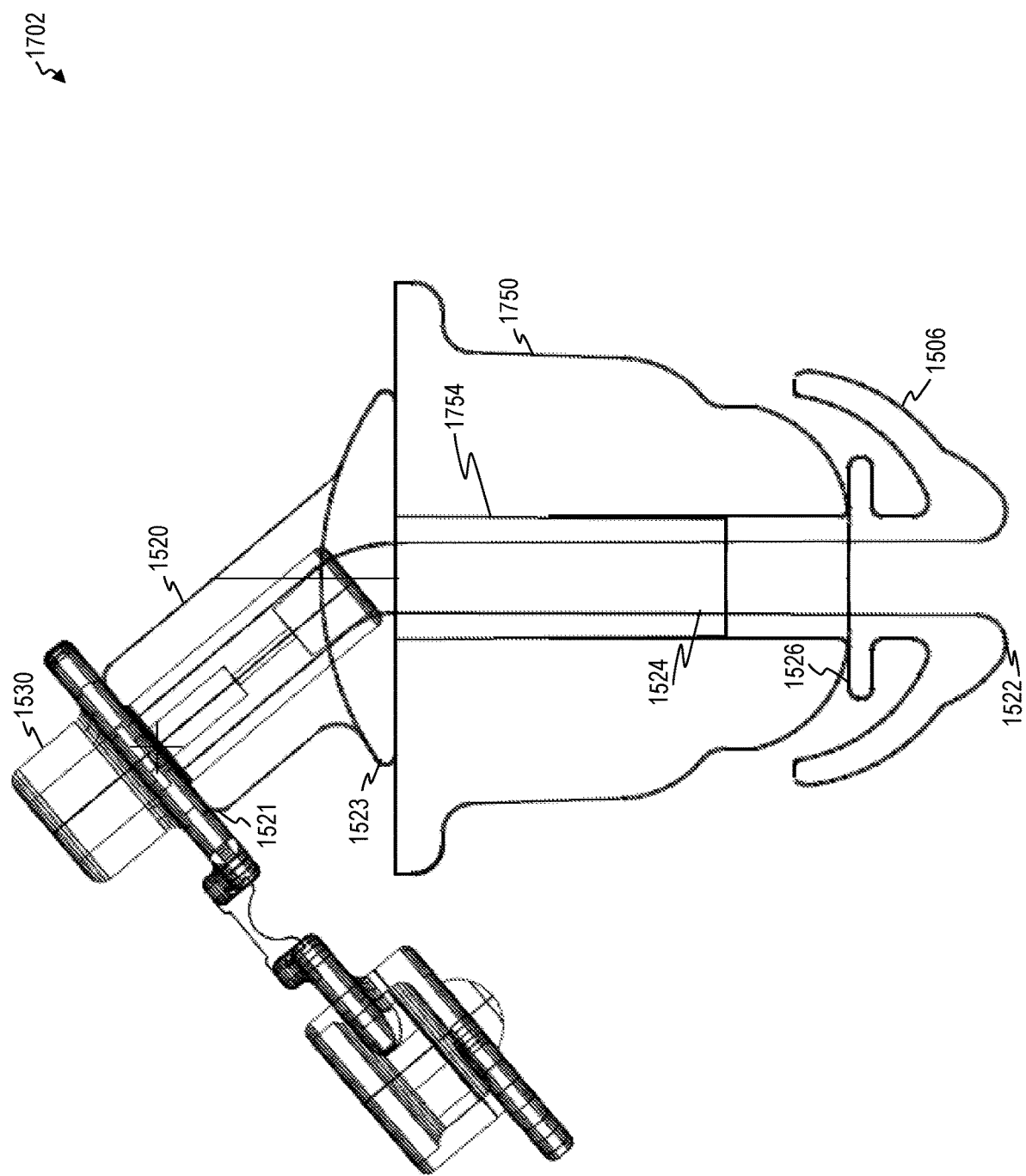

FIG. 2 is a back view of the earpiece device, according to some embodiments of the present invention.

FIG. 3 is a front view of the earpiece device, according to some embodiments of the present invention.

FIG. 4 is a left-side view of the earpiece device, according to some embodiments of the present invention.

FIG. 5 is a right-side view of the earpiece device, according to some embodiments of the present invention.

FIG. 6 is a bottom view of the earpiece device, according to some embodiments of the present invention.

FIG. 7 is a top view of the earpiece device, according to some embodiments of the present invention.

Figure 8:
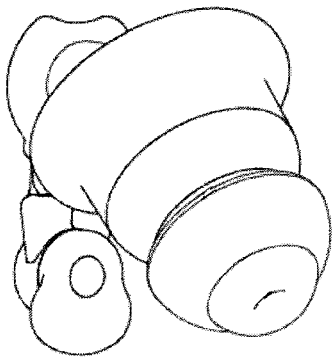
FIG. 8 is a perspective view of an earpiece device assembly, according to some embodiments of the present invention.

FIG. 8 is a perspective view of an earpiece device assembly, according to some embodiments of the present invention.

Figure 9:
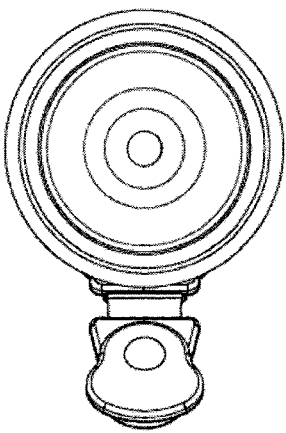
FIG. 9 is a bottom view of the earpiece device assembly, according to some embodiments of the present invention.

FIG. 9 is a bottom view of the earpiece device assembly, according to some embodiments of the present invention.

Figure 10:
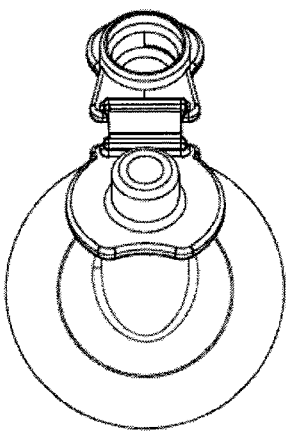
FIG. 10 is a top view of the earpiece device assembly, according to some embodiments of the present invention.

FIG. 10 is a top view of the earpiece device assembly, according to some embodiments of the present invention.

Figure 11:
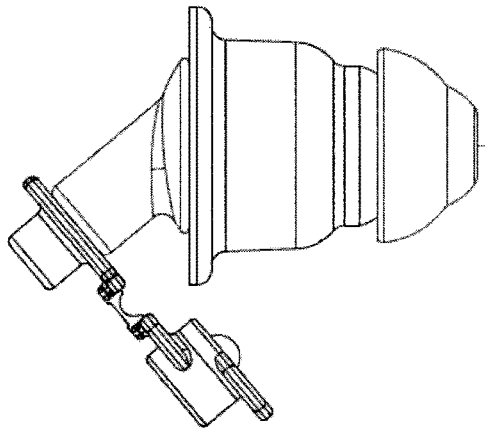
FIG. 11 is a left-side view of the earpiece device assembly, according to some embodiments of the present invention.

FIG. 11 is a left-side view of the earpiece device assembly, according to some embodiments of the present invention.

Figure 12:
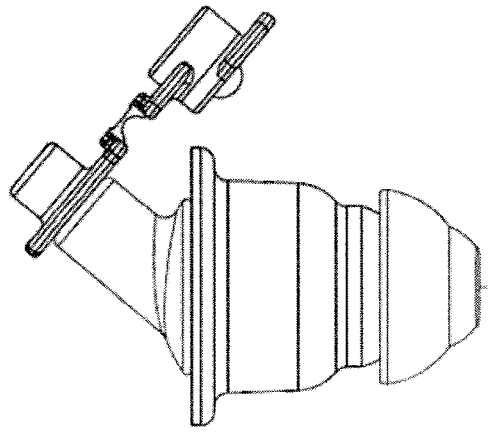
FIG. 12 is a right-side view of the earpiece device assembly, according to some embodiments of the present invention.

FIG. 12 is a right-side view of the earpiece device assembly, according to some embodiments of the present invention.

Figure 13:
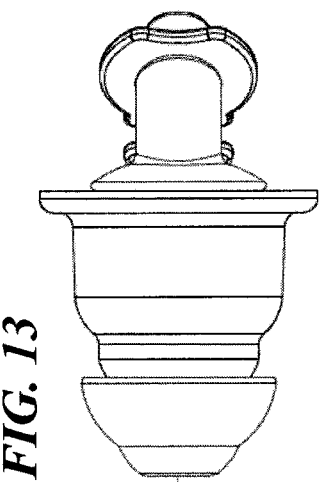
FIG. 13 is a front view of the earpiece device assembly, according to some embodiments of the present invention.

FIG. 13 is a front view of the earpiece device assembly, according to some embodiments of the present invention.

Figure 14:
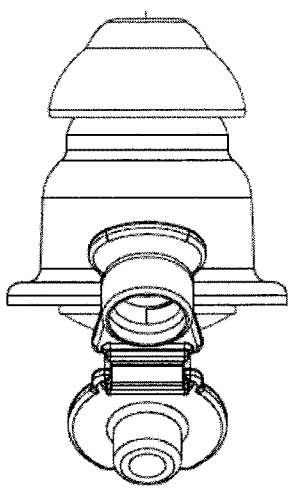
FIG. 14 is a back view of the earpiece device assembly, according to some embodiments of the present invention.

FIG. 14 is a back view of the earpiece device assembly, according to some embodiments of the present invention.

Figure 15:
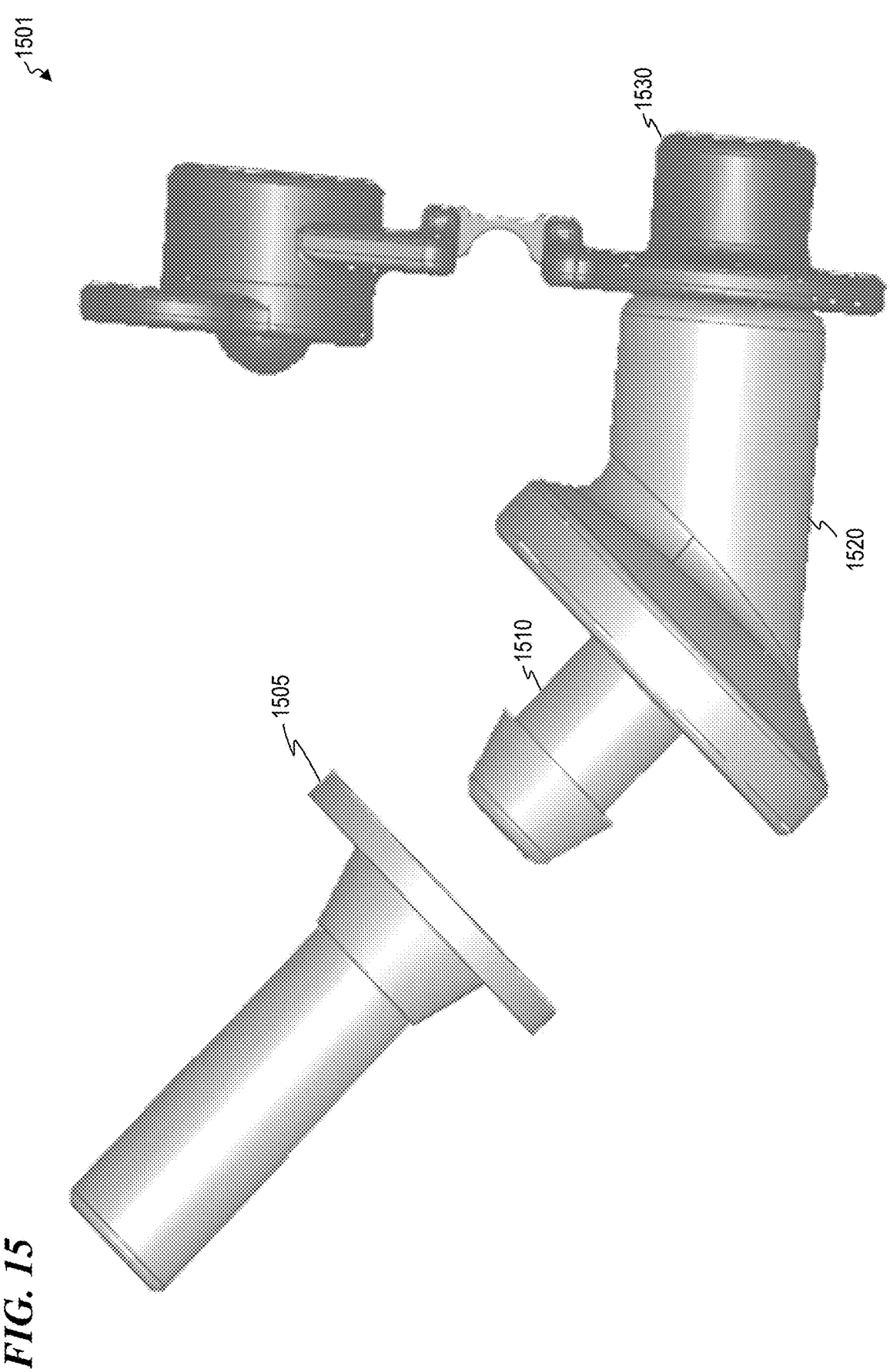
FIG. 15 is a partially exploded side view of an angled earpiece system 1501, according to some embodiments of the present invention.

FIG. 15 is a partially exploded side view of an angled earpiece system 1501, according to some embodiments of the present invention. In some embodiments, earpiece system 1501 includes a base 1520 having a barbed stem 1510, a sound filter 1530 that fits into an opening of base 1520 on a side of base 1520 that faces away from the inner ear of the user, and an adapter sleeve 1505 that fits onto (e.g., snaps onto) barbed stem 1510. In some embodiments, barbed stem 1510 is made separately from base 1520 and then coupled to base 1520. In some embodiments, sound filter 1530 is similar to the sound filters described in U.S. Pat. No. 9,603,746, which is introduced and incorporated by reference above. In some embodiments, system 1501 includes a channel (not shown) that runs through an entirety of system 1501 such that sound can pass through system 1501 via the channel (in some such embodiments, the cap of sound filter 1530 can be moved between an open position that allows sound to pass through system 1501 and a closed position that blocks sound from passing through system 1501). In some embodiments, there are no channels through system 1501 (e.g., in some such embodiments, system 1501 provides a full block against sound). In some embodiments, sound filter 1530 is replaced with a handle (see, e.g., handle 1831 of FIG. 18A). In some embodiments, earpiece system 1501 is configured to be placed into the ear such that adapter sleeve 1505 is located in the ear canal and base 1520 protrudes out from the ear canal. In some embodiments, at least a portion of base 1520 is flexible (e.g., in some embodiments, the portion of base 1520 other than barbed stem 1510 has a durometer of 45 Shore A) such that it can bend in order to avoid user discomfort when the earpiece system 1501 is in place in the ear and the user wears a helmet or other head covering that covers the user's ear.

In some embodiments, the longitudinal axis of barbed stem 1510 forms an angle with the longitudinal axis of sound filter 1530 (in some such embodiments, this angle provides a more natural fit in the user's ear for earpiece system 1501). In some embodiments, the angle formed by the bend in base 1520 is between approximately 20 and 70 degrees. In some embodiments, the angle is between 20 and 30 degrees; in some embodiments, between 30 and 40 degrees; in some embodiments, between 40 and 50 degrees; in some embodiments, between 50 and 60 degrees; in some embodiments, between 60 and 70 degrees. In some embodiments, the angle is 20 degrees. In some embodiments, the angle is 70 degrees.

Figure 16B:
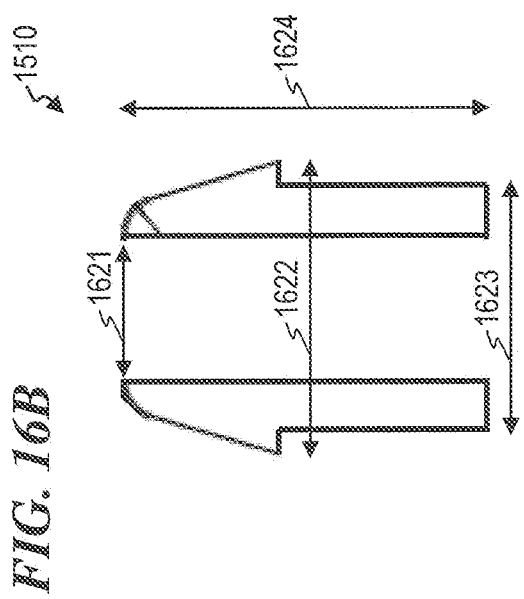
FIG. 16B is a schematic diagram of barbed stem 1510, according to some embodiments of the present invention.
Figure 16A:
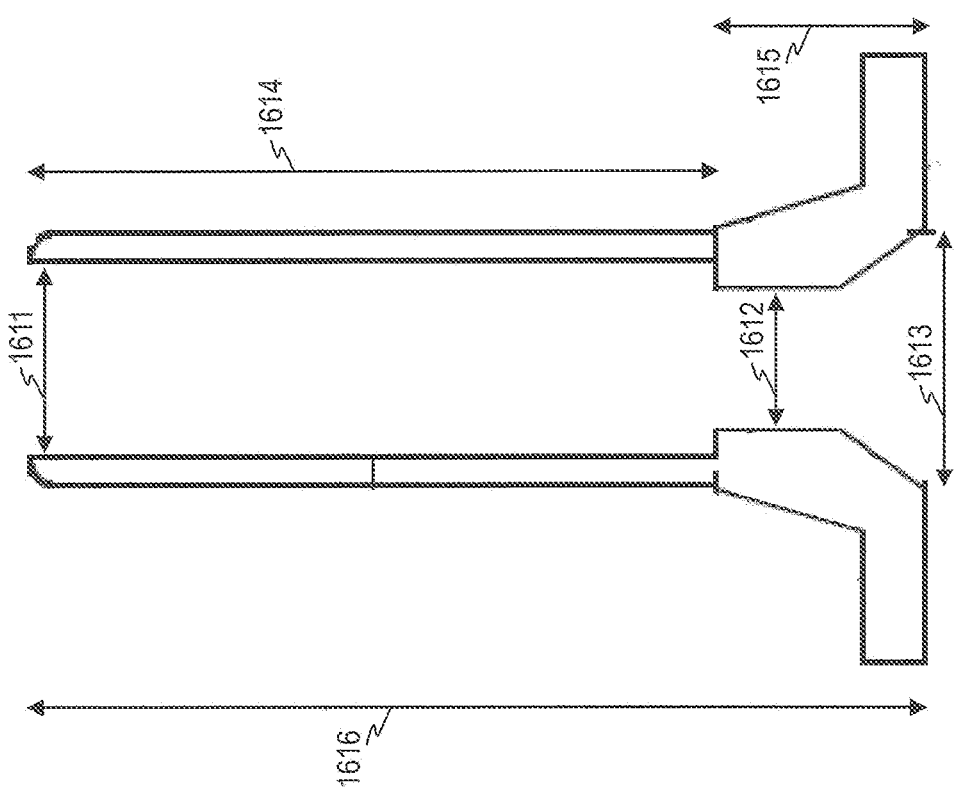
FIG. 16A is a schematic diagram of adapter sleeve 1505, according to some embodiments of the present invention.

FIG. 16A is a schematic diagram of adapter sleeve 1505, according to some embodiments of the present invention. In some embodiments, adapter sleeve 1505 is made of soft (e.g., 70 Shore A durometer) polyvinyl chloride (PVC). In some embodiments, an ear-canal component (also referred to herein as an eartip) that is configured to be placed into the ear canal is placed over sleeve 1505 and sleeve 1505 is then snapped onto barbed stem 1510 of base 1520. In some such embodiments, a foam eartip is placed over and glued to sleeve 1505. In other such embodiments, a PVC eartip having a durometer of 35 Shore A is placed over and solvent bonded to sleeve 1505. In some embodiments, as shown in FIG. 16A, adapter sleeve 1505 has a channel that passes completely through sleeve 1505 such that sound can pass through sleeve 1505 as part of an overall earpiece system that allows sound to pass through. In other embodiments, adapter sleeve 1505 includes the opening at the bottom with diameters 1613 and 1612 in order to receive stem 1510, but otherwise sleeve 1505 does not include a channel and instead provides a full block against sound passing through.

In some embodiments, adapter sleeve 1505 includes a first diameter 1611 (e.g., in some embodiments, 0.0940 inches), a second diameter 1612 (e.g., in some embodiments, 0.0680 inches), a third diameter 1613 (e.g., in some embodiments, 0.1250 inches), a first height 1614 (e.g., in some embodiments, 0.3267 inches), a second height 1615 (e.g., in some embodiments, 0.0993 inches), and an overall height 1616 (e.g., in some embodiments, 0.4260 inches).

FIG. 16B is a schematic diagram of barbed stem 1510, according to some embodiments of the present invention. In some embodiments, barbed stem 1510 is made of rigid (e.g., 95 Shore A) PVC. In some embodiments, stem 1510 includes a first diameter 1621 (e.g., in some embodiments, 0.070 inches), a second diameter 1622 (e.g., in some embodiments, 0.140 inches), and a third diameter 1623 (e.g., in some embodiments, 0.117 inches). In some embodiments, as shown in FIG. 16B, barbed stem 1510 has a channel that passes completely through stem 1510 such that sound can pass through stem 1510 as part of an overall earpiece system that allows sound to pass through. In other embodiments, barbed stem 1510 does not include a channel and instead provides a full block against sound passing through.

FIG. 17A is a side view of an angled earpiece system 1701, according to some embodiments of the present invention. In some embodiments, earpiece system 1701 is substantially similar to earpiece system 1501 of FIG. 15 except that an eartip 1740 is placed onto adapter sleeve 1505 and adapter sleeve 1505 is fit onto base 1520 (via stem 1510, which is not shown in FIG. 17A). In some embodiments, eartip 1740 is a bell-shaped foam eartip that is glued onto sleeve 1505.

FIG. 17B-1 is a side view of an angled earpiece system 1702, according to some embodiments of the present invention. In some embodiments, earpiece system 1701 is substantially similar to earpiece system 1501 of FIG. 15 except that an eartip 1750 is placed onto adapter sleeve 1505, flange 1506 is inserted onto the end of sleeve 1505 to help hold eartip 1750 in place, and adapter sleeve 1505 is fit onto base 1520 (via stem 1510, which is not shown in FIG. 17B). In some embodiments, flange 1506 has a durometer of 35 Shore A (e.g., in some embodiments, flange 1506 is made from PVC having a durometer of 35 Shore A).

FIG. 17B-2 is a schematic cross-sectional diagram of angled earpiece system 1702, according to some embodiments of the present invention. In some embodiments, base 1520 includes an emitter end 1522, a receiver end 1521, a flange 1523, and a channel 1524 that passes through an entire length of base 1520. In some embodiments, flange 1506 includes a stop 1526 that is located within the cup shape of flange 1506. In some embodiments, eartip 1750 includes a channel 1754 that passes through an entire length of eartip 1750.

Figure 17C:
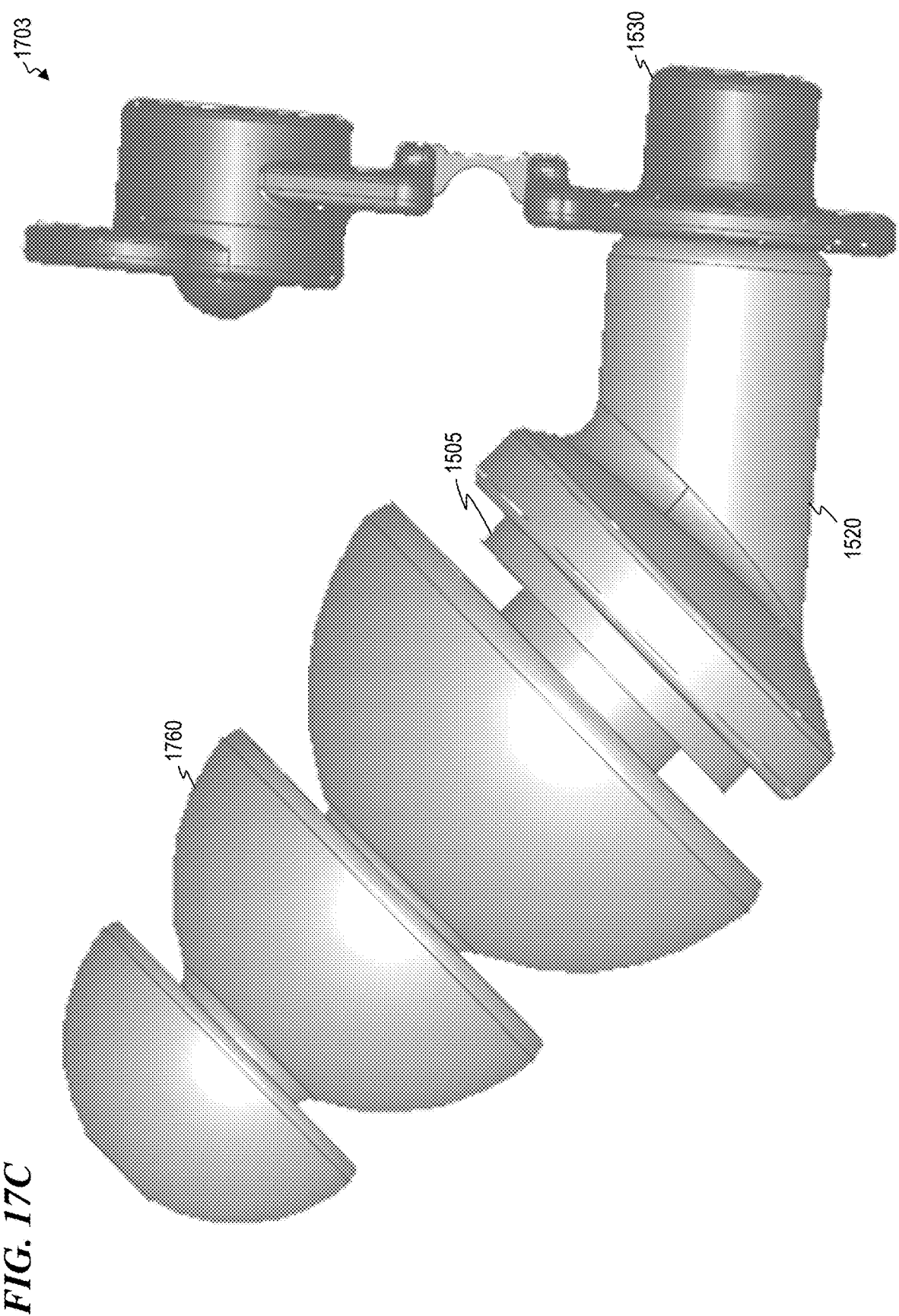
FIG. 17C is a side view of an angled earpiece system 1703, according to some embodiments of the present invention.

FIG. 17C is a side view of an angled earpiece system 1703, according to some embodiments of the present invention. In some embodiments, earpiece system 1701 is substantially similar to earpiece system 1501 of FIG. 15 except that an eartip 1760 is placed onto adapter sleeve 1505 and adapter sleeve 1505 is fit onto base 1520 (via stem 1510, which is not shown in FIG. 17A) and. In some embodiments, eartip 1760 includes a series of three different-sized cup shapes (in some embodiments, having a convex outer surface and a concave back-side or inner surface) that are made of PVC, foam, or any other suitable material. In some embodiments, earpiece system 1701 does not include adapter sleeve 1505 and eartip 1760 instead fits directly onto barbed stem 1510 shown in FIG. 15.

FIG. 18A is an exploded side view of an angled earpiece system 1801, according to some embodiments of the present invention. In some embodiments, system 1801 includes a handle 1831 that fits into base 1820 on a first side of base 1820 (in some such embodiments, the stem of handle 1831 inserts into a ring-shaped channel 1821 in base 1820). In some embodiments, handle 1831 is configured to be held between the index finger and thumb of the user. In some embodiments, base 1820 includes a coupler 1805 on the opposite second side of base 1820, and in some embodiments, coupler 1804 couples to an eartip 1840 via a channel 1841 of eartip 1840. In some embodiments, coupler 1805 is an adapter sleeve such as adapter sleeve 1505 of FIG. 15 (in other embodiments, coupler 1805 is a stem that is integral with base 1820). In some embodiments, system 1801 is substantially similar to system 1501 of FIG. 15 except that sound filter 1530 is replaced by handle 1831.

FIG. 18B is an exploded and rotated side view of angled earpiece system 1801, according to some embodiments of the present invention.

Figure 18C:
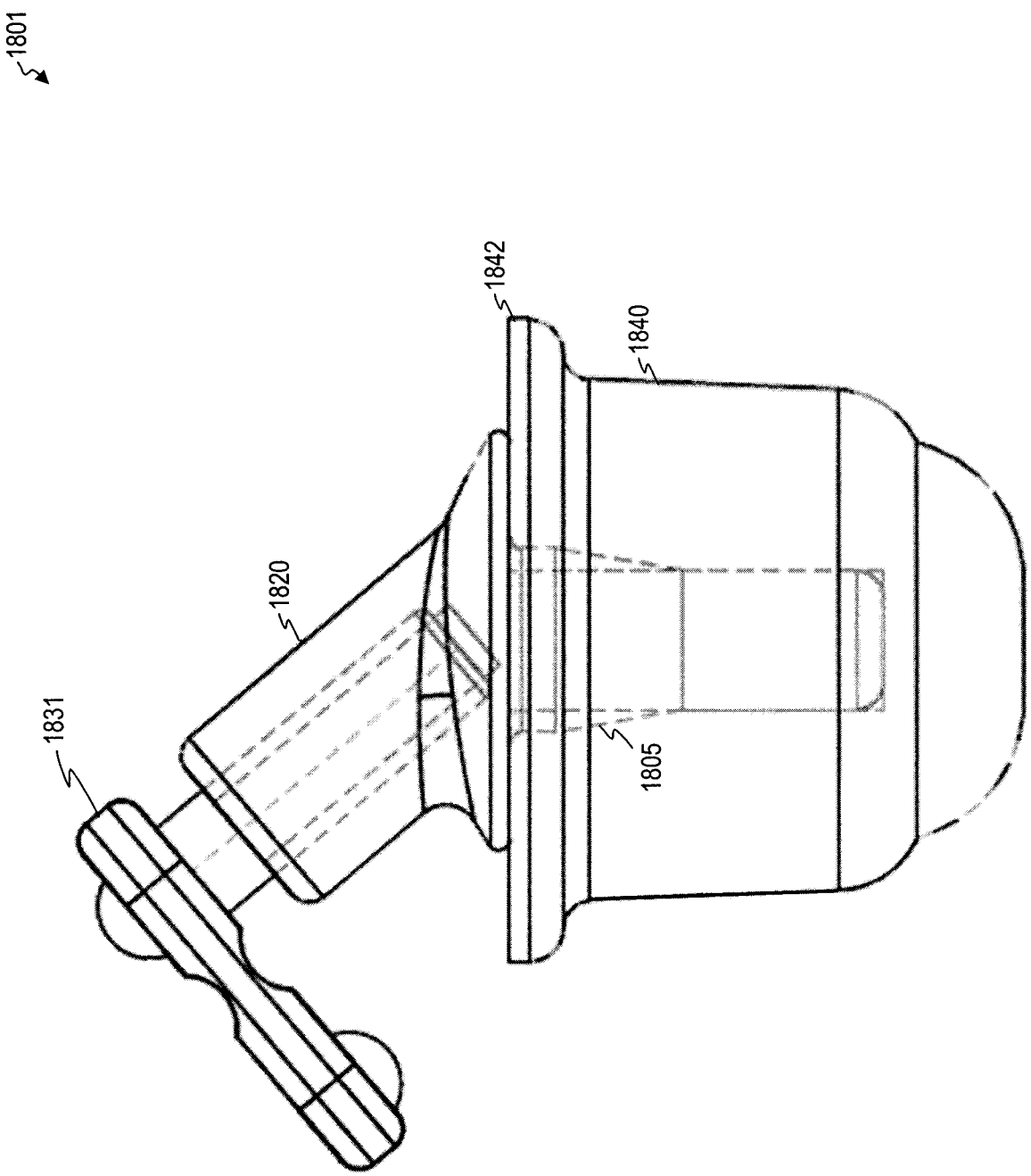
FIG. 18C is an assembled side view of angled earpiece system 1801, according to some embodiments of the present invention.

FIG. 18C is an assembled side view of angled earpiece system 1801, according to some embodiments of the present invention. In some embodiments, the lip 1842 of eartip 1840 functions as a tragus lock that holds eartip 1840 in the ear canal when system 1801 is used (in some such embodiments, eartip 1840 is prevented from falling out of the ear canal by lip 1842 pressing against the ear-canal side of the user's tragus). In some embodiments of system 1801, eartip 1740 of FIG. 17A is substituted for eartip 1840.

Figure 19B:
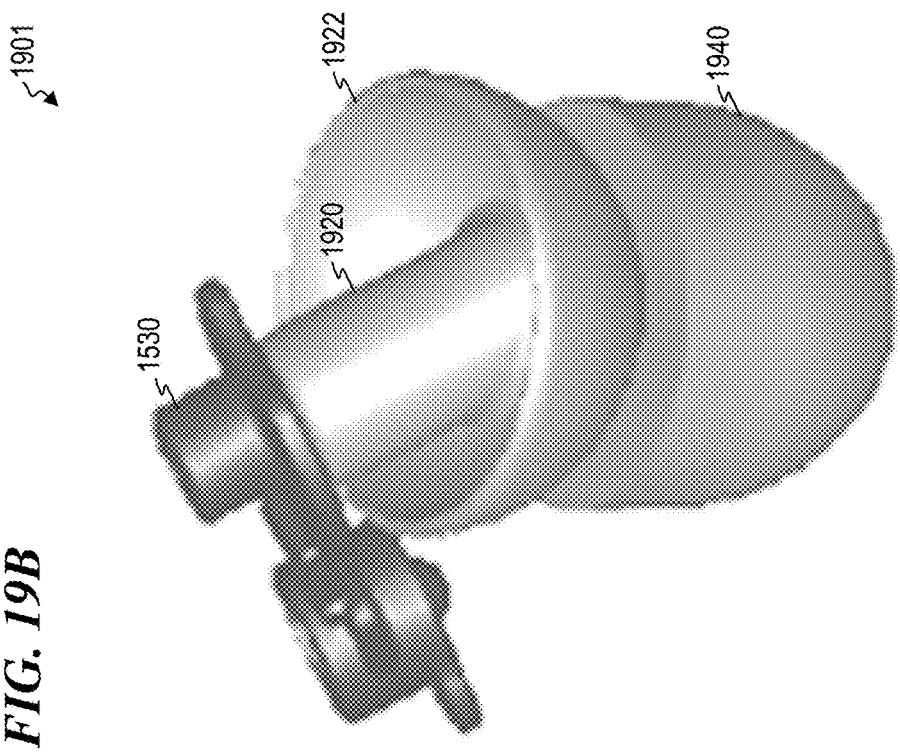
FIG. 19B is a perspective view of angled earpiece system 1901, according to some embodiments of the present invention.
Figure 19A:
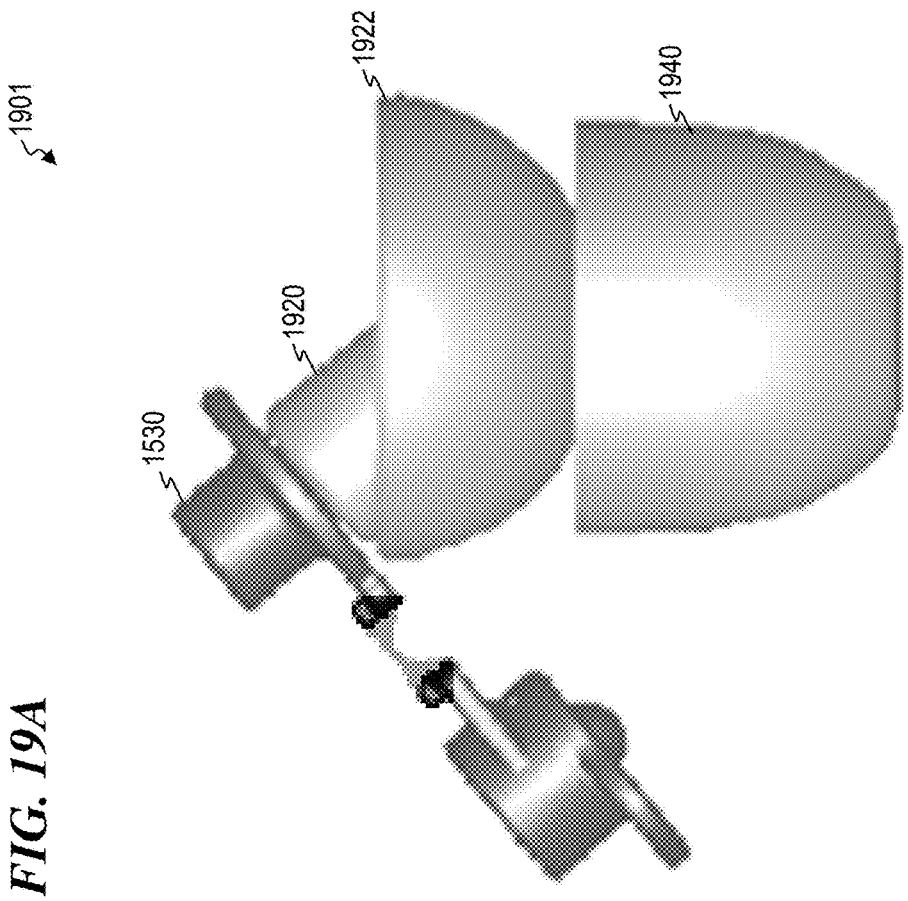
FIG. 19A is a side view of an angled earpiece system 1901, according to some embodiments of the present invention.

FIG. 19A is a side view of an angled earpiece system 1901, according to some embodiments of the present invention. In some embodiments, system 1901 includes a base 1920 having a cup 1922, a sound filter 1530 that fits into base 1920, and an eartip 1940 that couples to a stem (not shown) protruding from the bottom of cup 1922. In some embodiments, earpiece system 1901 is configured to be placed into the ear such that eartip 1940 is located in the ear canal and base 1520 (including cup 1922) protrudes out from the ear canal. In some embodiments, eartip 1940 is a bell-shaped foam eartip that is glued onto the stem of base 1920.

FIG. 19B is a perspective view of angled earpiece system 1901, according to some embodiments of the present invention.

Figure 19D:
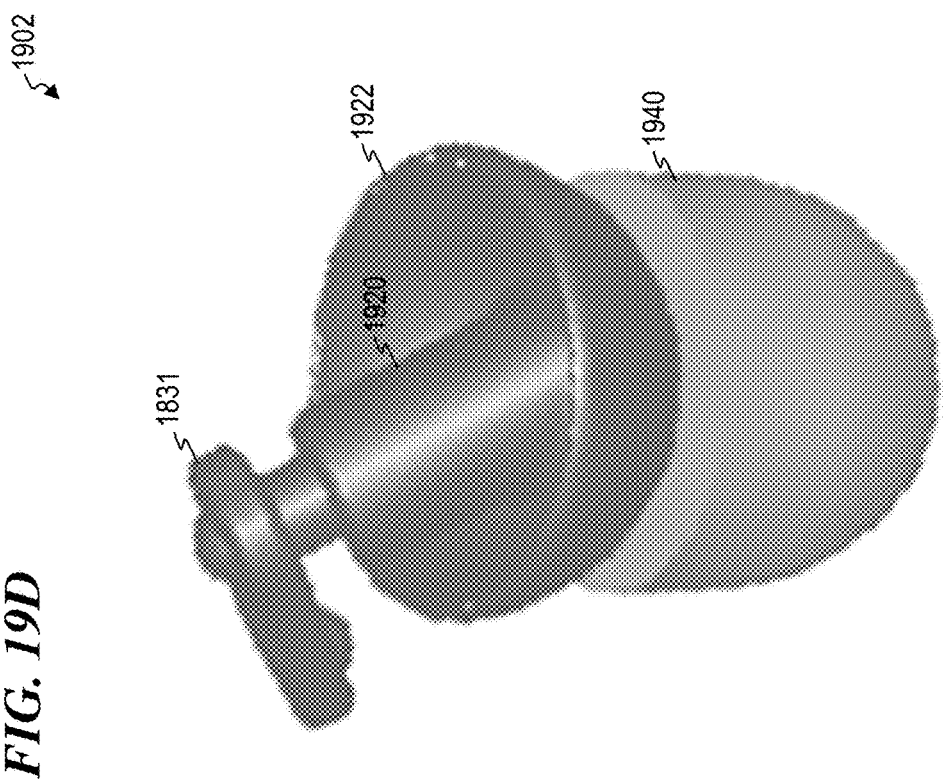
FIG. 19D is a perspective view of angled earpiece system 1902, according to some embodiments of the present invention.
Figure 19C:
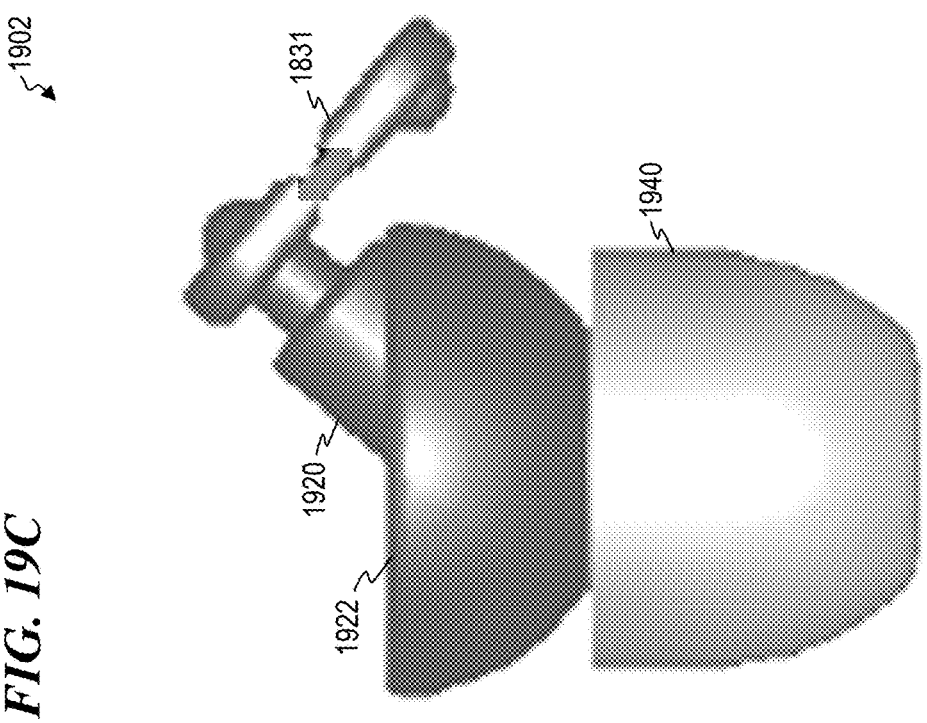
FIG. 19C is a side view of an angled earpiece system 1902, according to some embodiments of the present invention.

FIG. 19C is a side view of an angled earpiece system 1902, according to some embodiments of the present invention. In some embodiments, system 1902 is substantially similar to system 1901 of FIG. 19A except that sound filter 1530 is replaced by handle 1831.

FIG. 19D is a perspective view of angled earpiece system 1902, according to some embodiments of the present invention.

In some embodiments, the present invention provides a sound attenuation system that includes a base having a first portion on an emitter end of the base and a second portion on a receiver end of the base, wherein the first portion has a first longitudinal axis, wherein the second portion has a second longitudinal axis, and wherein the first longitudinal axis is at a first angle to the second longitudinal axis; an adapter having a first end and a second end; a sound-attenuation plug, wherein the first end of the adapter is configured to couple to the sound-attenuation plug, and wherein the second end of the adapter is configured to couple to the first portion of the base; and a receiver-end component configured to insert into the second portion of the base.

In some embodiments of the system, the receiver-end component includes a handle.

In some embodiments, the system includes a channel that runs through the base, the adapter, the sound-attenuation plug, and the receiver-end component such that sound can pass through the system, and wherein the receiver-end component includes a cap that has a first position in which the cap occludes the channel and a second position in which the cap is clear of the channel.

In some embodiments of the system, the sound-attenuation plug includes a foam body having a cavity that is configured to fit over the first end of the adapter to couple the foam body to the first end of the adapter.

In some embodiments, the sound-attenuation plug includes a foam body having a cavity that is configured to fit over the first end of the adapter to couple the foam body to the first end of the adapter, the system further including a flange configured to couple to the first end of the adapter after the foam body is coupled to the adapter such that the foam body is located between the flange and the base when the adapter is coupled to the base.

In some embodiments of the system, the first portion of the base includes a barbed stem having a first durometer, wherein the second end of the adapter includes a cavity having a second durometer, and wherein the cavity of the second end of the adapter is configured to snap onto the barbed stem of the first portion of the base.

In some embodiments, the sound-attenuation plug includes a plurality of cup-shaped components including a first cup-shaped component and a second cup-shaped component, wherein the first cup-shaped component has a first diameter, wherein the second cup-shaped component has a second diameter, and wherein the first diameter is smaller than the second diameter.

In some embodiments, the angle between the first longitudinal axis and the second longitudinal axis is between approximately twenty (20) and seventy (70) degrees, inclusive.

In some embodiments, the angle between the first longitudinal axis and the second longitudinal axis is between approximately thirty (30) and seventy (60) degrees, inclusive.

In some embodiments, the angle between the first longitudinal axis and the second longitudinal axis is between approximately forty (40) and fifty (50) degrees, inclusive.

In some embodiments, the angle between the first longitudinal axis and the second longitudinal axis is about forty-five (45) degrees.

In some embodiments, the present invention provides a sound attenuation system that includes a base having a first portion on an emitter end of the base and a second portion on a receiver end of the base, wherein the first portion has a first longitudinal axis, wherein the second portion has a second longitudinal axis, and wherein the first longitudinal axis is at a first angle to the second longitudinal axis; a sound-attenuation plug, wherein the sound-attenuation plug is configured to couple to the first portion of the base; and a receiver-end component configured to insert into the second portion of the base.

In some embodiments of the system, the first portion of the base includes a stem, wherein the stem is configured to insert into a cavity of the sound-attenuation plug to couple the sound-attenuation plug to the base, and wherein the base includes a cup-shaped component located in between the stem of the base and the second portion of the base.

In some embodiments, the system includes a channel that runs through the base, the sound-attenuation plug, and the receiver-end component such that sound can pass through the system, and wherein the receiver-end component includes a cap that has a first position in which the cap occludes the channel and a second position in which the cap is clear of the channel.

In some embodiments, the present invention provides a method of making a sound-attenuation system, the method including forming a base having a first portion on an emitter end of the base and a second portion on a receiver end of the base, wherein the first portion has a first longitudinal axis, wherein the second portion has a second longitudinal axis, wherein the first longitudinal axis is at a first angle to the second longitudinal axis, and wherein the first portion of the base has a first durometer and the second portion of the base has a second durometer; generating an adapter having a first end and a second end, wherein the adapter has a third durometer; creating a receiver-end component; providing a sound-attenuation plug; coupling the first end of the adapter to the sound-attenuation plug; fastening the second end of the adapter onto the first portion of the base; and inserting the receiver-end component into the second portion of the base.

In some embodiments of the method, the first portion of the base includes a barbed stem, wherein the second end of the adapter includes a cavity, and wherein the fastening includes snapping the cavity of the second end of the adapter onto the barbed stem of the first portion of the base.

In some embodiments, the creating of the receiver-end component includes forming a handle.

In some embodiments, the coupling of the first end of the adapter to the sound-attenuation plug includes inserting the first end of the adapter into a cavity in the sound-attenuation plug and gluing the cavity of the sound-attenuation plug to the first end of the adapter.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A sound-attenuation system for placement at least partially in an ear canal of a person, the system comprising:
   a base having an emitter end and a receiver end, wherein the base includes:
      a first flange at the emitter end of the base, wherein the first flange has a cup shape having a convex external surface at the emitter end of the base and an outer perimeter, wherein the cup shape is configured to engage the ear canal to create a seal in the ear canal, wherein the first flange has a concave inner surface toward the receiver end of the base,
      a stop located within the cup shape of the first flange;
   a sound-attenuation plug having a distal end and a proximal end, wherein the sound-attenuation plug includes a first channel that passes through an entire length of the sound-attenuation plug, wherein the sound-attenuation plug is configured to couple to the base such that the distal end of the sound-attenuation plug is adjacent to the stop and at least a portion of the sound-attenuation plug is within the outer perimeter of the cup shape of the first flange.

2. The sound-attenuation system of claim 1, wherein the base includes a second flange, and wherein the proximal end of the sound-attenuation plug is adjacent to the second flange.

3. The sound-attenuation system of claim 1, wherein the base includes a second channel that passes through an entire length of the base.

4. The sound-attenuation system of claim 1, wherein a portion of the base is tapered and has an outer diameter that decreases from the receiver end of the base to the emitter end of the base.

5. The sound-attenuation system of claim 1, wherein the sound-attenuation plug includes a foam body.

6. The sound-attenuation system of claim 1, wherein the receiver end of the base has a first longitudinal axis, wherein the emitter end of the base has a second longitudinal axis, and wherein the first longitudinal axis is at a first angle between approximately 20 and 70 degrees relative to the second longitudinal axis.

7. The sound-attenuation system of claim 1, wherein the base further includes:
   a barbed stem; and
   an adapter sleeve having an emitter end and a receiver end, wherein the adapter sleeve is configured to couple to the barbed stem such that the emitter end of the adapter sleeve forms the emitter end of the base, wherein the adapter sleeve is configured to insert into the first channel of the sound-attenuation plug such that the sound-attenuation plug is coupled to the base, and wherein the first flange is configured to couple to the emitter end of the adapter sleeve.

8. The sound-attenuation system of claim 1, wherein the first flange is made from polyvinyl chloride (PVC) having a durometer of 35 Shore A.

9. The sound-attenuation system of claim 1, further comprising:
   a sound filter configured to insert into the receiver end of the base, wherein the sound filter has a channel extending from an inlet end to an outlet end, wherein the sound filter is coupled to a cap by a joint, and wherein the joint is configured to allow the cap to have a first position in which the cap occludes the channel and to have a second position in which the cap is clear of the channel.

10. The sound-attenuation system of claim 1, further comprising:
    a handle configured to insert into the receiver end of the base, wherein the handle is configured to be held by the person such that the sound-attenuation system can be inserted into the ear canal of the person.

11. A method for assembling a sound-attenuation earplug, the method comprising:
    forming a base having an emitter end and a receiver end, wherein the base includes:
       a first flange at the emitter end of the base, wherein the first flange has a cup shape having a convex external surface at the emitter end of the base and an outer perimeter, wherein the cup shape is configured to engage the ear canal to create a seal in the ear canal, wherein the first flange has a concave inner surface toward the receiver end of the base,
       a stop located within the cup shape of the first flange;
    forming a sound-attenuation plug having a distal end and a proximal end, wherein the sound-attenuation plug includes a first channel that passes through an entire length of the sound-attenuation plug; and
    forming the sound-attenuation earplug by coupling the sound-attenuation plug to the base such that the distal end of the sound-attenuation plug is adjacent to the stop and such that at least a portion of the sound-attenuation plug is within the outer perimeter of the cup shape of the first flange.

12. The method of claim 11, wherein the sound-attenuation plug includes a foam body.

13. The method of claim 11, wherein the receiver end of the base has a first longitudinal axis, wherein the emitter end of the base has a second longitudinal axis, and wherein the first longitudinal axis is at a first angle relative to the second longitudinal axis.

14. The method of claim 11, wherein the forming of the base includes forming a second flange, wherein the proximal end of the sound-attenuation plug is adjacent to the second flange.

15. The method of claim 11, wherein the sound-attenuation earplug includes a second channel that passes through an entire length of the sound-attenuation earplug.

16. The method of claim 11, wherein the forming of the base includes tapering a portion of the base such that an outer diameter of the base decreases from the receiver end of the base to the emitter end of the base.

17. The method of claim 11, wherein the forming of the base includes:
    forming a barbed stem;
    forming an adapter sleeve having an emitter end and a receiver end; and coupling the adapter sleeve to the barbed stem such that the emitter end of the adapter sleeve forms the emitter end of the base;

wherein the forming of the sound-attenuation earplug includes inserting the adapter sleeve into the first channel of the sound-attenuation plug, the method further comprising:

coupling the first flange to the emitter end of the adapter sleeve.

18. The method of claim 11, wherein the first flange is made from polyvinyl chloride (PVC) having a durometer of 35 Shore A.

19. The method of claim 11, further comprising:

forming a handle;

inserting the handle into the receiver end of the base, wherein the handle is configured to be held by the person such that the sound-attenuation system can be inserted into the ear canal of the person.

20. The method of claim 11, further comprising:

forming a sound filter;

inserting the sound filter into the receiver end of the base, wherein the sound filter has a channel extending from an inlet end to an outlet end, wherein the sound filter is coupled to a cap by a joint, and wherein the joint is configured to allow the cap to have a first position in which the cap occludes the channel and to have a second position in which the cap is clear of the channel.

\* \* \* \* \*